US012239780B2

(12) United States Patent
Fröhlich et al.

(10) Patent No.: US 12,239,780 B2
(45) Date of Patent: Mar. 4, 2025

(54) BI-DOSE NASAL SPRAY

(71) Applicant: AKROSWISS AG, Zug (CH)

(72) Inventors: Johannes Malte Fröhlich, Zollikon (CH); Matthias Gergely Zadory, Dietikon (CH); Stefan Pascal Biendl, Basel (CH)

(73) Assignee: AKROSWISS AG, Zug (CH)

( * ) Notice: Subject to any disclaimer, the term of this patent is extended or adjusted under 35 U.S.C. 154(b) by 1064 days.

(21) Appl. No.: 17/053,284

(22) PCT Filed: May 8, 2019

(86) PCT No.: PCT/EP2019/061827
§ 371 (c)(1),
(2) Date: Nov. 5, 2020

(87) PCT Pub. No.: WO2019/215235
PCT Pub. Date: Nov. 14, 2019

(65) Prior Publication Data
US 2021/0361884 A1      Nov. 25, 2021

(30) Foreign Application Priority Data

May 8, 2018   (CH) .................................. 00575/18
Dec. 3, 2018  (EP) .................................. 18209897

(51) Int. Cl.
*A61M 15/08*   (2006.01)
*A61K 31/5517* (2006.01)
*A61M 11/00*   (2006.01)

(52) U.S. Cl.
CPC ....... *A61M 11/007* (2014.02); *A61K 31/5517* (2013.01); *A61M 15/08* (2013.01); *A61M 2209/02* (2013.01)

(58) Field of Classification Search
CPC .......................... A61M 11/007; A61M 15/08; A61M 2209/02; A61M 15/0086; A61M 15/009;

(Continued)

(56) References Cited

U.S. PATENT DOCUMENTS 3,022,619 A    2/1962   Strong et al.
3,292,342 A    12/1966  Kapeker
(Continued)

FOREIGN PATENT DOCUMENTS

DE    199 09 995 A1    9/2000
DE    102012008397     10/2013
(Continued)

OTHER PUBLICATIONS

Topical contrast agents to improve soft-tissue contrast in the upper airway using cone beam CT: a pilot study (Year: 2013).*

(Continued)

*Primary Examiner* — Annette Dixon
(74) *Attorney, Agent, or Firm* — WOMBLE BOND DICKINSON (US) LLP

(57) ABSTRACT

A nasal spray containing an aqueous solution or a fluid with an anxiolytic or anticonvulsant substance, wherein the nasal spray is characterized in that with the nasal spray, two sprays with each an equivalent, defined volume of the aqueous solution or liquid of the active agent, can be intranasally administered to a patient. The nasal spray allows for an administration, independent of the spatial orientation of the nasal spray in any position of the patient (standing upright, sitting, lying or in any intermediate position). The nasal spray can be used directly without prior activation. It is apparent from the nasal spray whether a spray or even a second spray has been made with the nasal spray. A spray can be administered one-handed by the patient or a third person. The active agent is midazolam or a salt thereof.

9 Claims, 5 Drawing Sheets

Figure 1:
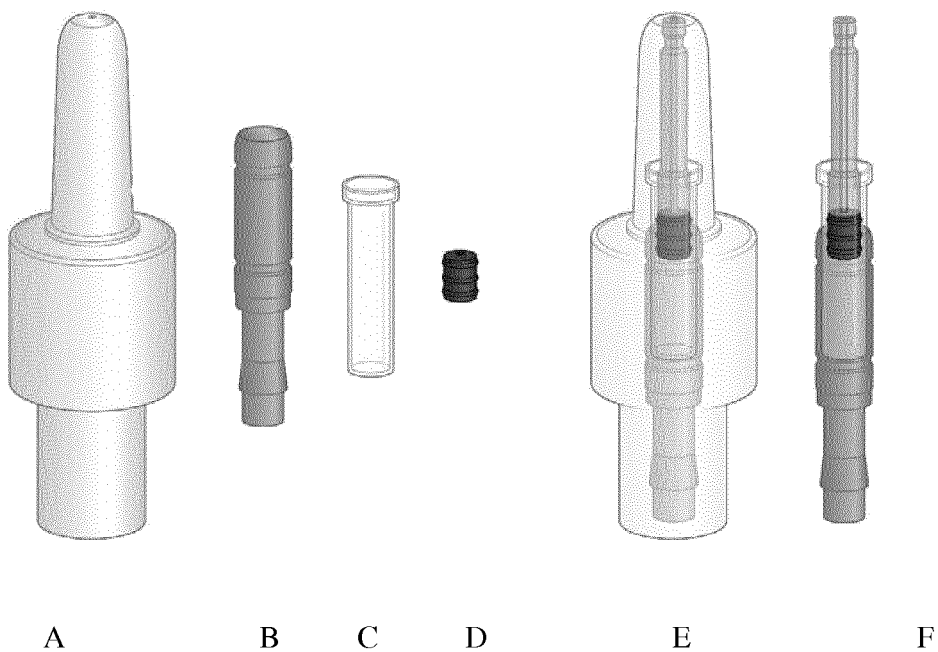

(58) Field of Classification Search
CPC ........ A61M 11/001; A61M 2005/3114; A61M 2207/00; A61M 2205/21; A61M 2209/045; A61M 15/0071; A61M 11/00; A61M 11/003; A61M 11/006; A61M 11/02; A61M 11/06; A61M 13/00; A61M 15/00; A61M 15/0003; A61M 15/0006; A61M 15/0028; A61M 15/003; A61M 15/0031; A61M 15/0035; A61M 15/0036; A61M 15/0038; A61M 15/004; A61M 15/0041; A61M 15/0045; A61M 15/0048; A61M 15/005; A61M 15/0051; A61M 15/0065; A61M 15/0066; A61M 15/0068; A61M 15/008; A61M 15/0081; A61M 15/0083; A61M 15/0091; A61M 16/161; A61M 2202/0007; A61M 2202/0468; A61M 2202/062; A61M 2202/064; A61M 2205/0266; A61M 2205/073; A61M 2205/075; A61M 2205/14; A61M 2205/19; A61M 2205/276; A61M 2205/3368; A61M 2205/35; A61M 2205/42; A61M 2205/50; A61M 2205/502; A61M 2205/52; A61M 2205/58; A61M 2205/581; A61M 2205/582; A61M 2205/583; A61M 2205/584; A61M 2205/586; A61M 2205/587; A61M 2205/6081; A61M 2205/82; A61M 2205/8206; A61M 2205/8218; A61M 2206/10; A61M 2206/16; A61M 2210/0612; A61M 2210/0618; A61M 31/00; A61K 31/5517; A61K 2300/00; A61K 31/135; A61K 31/4045; A61K 31/485; A61K 45/06; A61K 47/02; A61K 47/18; A61K 47/186; A61K 9/0019; A61K 9/0043; A61K 9/08; A61K 9/12; G09B 23/30; G09B 23/285; A61F 9/0008; A61J 1/2093; A61P 25/04; A61P 25/08; A61P 25/22; B05B 11/0078; B05B 11/02; B05B 11/025; B05B 11/062; B05B 11/064; B05B 11/067; B05B 11/1005; B05B 11/1011; B05B 11/1081; B05B 11/1084; B65D 83/0005; B65D 83/38; G01F 11/24; G16H 20/13

See application file for complete search history.

(56) References Cited

U.S. PATENT DOCUMENTS

| | | | |
|---|---|---|---|
| 5,166,202 A * | 11/1992 | Schweizer | A61K 31/55 514/219 |
| 5,237,797 A | 8/1993 | Varlet | |
| 5,307,953 A * | 5/1994 | Regan | A61M 15/0036 604/203 |
| 5,469,989 A * | 11/1995 | Graf | A61M 15/0025 222/327 |
| 5,509,584 A | 4/1996 | Gueret | |
| 5,519,984 A | 5/1996 | Beussink et al. | |
| 5,813,570 A * | 9/1998 | Fuchs | B05B 11/0027 604/203 |
| 6,321,942 B1 * | 11/2001 | Krampen | B05B 15/652 222/320 |
| 6,382,465 B1 * | 5/2002 | Greiner-Perth | A61M 15/0081 222/326 |
| 6,446,839 B1 * | 9/2002 | Ritsche | A61M 15/0065 222/153.13 |
| 6,626,379 B1 | 9/2003 | Ritsche et al. | |
| 8,734,392 B2 * | 5/2014 | Stadelhofer | B05B 11/0027 128/200.14 |
| 10,940,274 B2 * | 3/2021 | Malhotra | A61M 15/004 |
| 11,478,809 B2 | 10/2022 | Adam | |
| 2002/0010198 A1 * | 1/2002 | Jerussi | A61K 31/50 514/340 |
| 2002/0092524 A1 * | 7/2002 | Lockhart | B05B 11/062 128/203.21 |
| 2004/0176359 A1 * | 9/2004 | Wermeling | A61K 47/10 514/221 |
| 2004/0235144 A1 | 11/2004 | Laurent et al. | |
| 2006/0168916 A1 | 8/2006 | Griebel et al. | |
| 2007/0175538 A1 | 8/2007 | Rothbauer et al. | |
| 2009/0274762 A1 | 11/2009 | Willis et al. | |
| 2009/0297441 A1 * | 12/2009 | Canham | A61K 49/06 424/9.4 |
| 2010/0113426 A1 | 5/2010 | Wermeling | |
| 2010/0145275 A1 | 6/2010 | Grunhut et al. | |
| 2010/0199606 A1 | 8/2010 | Behar et al. | |
| 2010/0212663 A1 | 8/2010 | Vedrine et al. | |
| 2011/0146207 A1 | 6/2011 | Desrues | |
| 2015/0013276 A1 | 1/2015 | Okajima et al. | |
| 2016/0068326 A1 | 3/2016 | Le Maner et al. | |
| 2016/0101249 A1 | 4/2016 | Djupesland et al. | |
| 2017/0081056 A1 | 3/2017 | Zambaux et al. | |
| 2017/0136477 A1 | 5/2017 | Heldt et al. | |
| 2017/0304568 A1 | 10/2017 | Francis et al. | |

FOREIGN PATENT DOCUMENTS

| | | | |
|---|---|---|---|
| DE | 10 2014 003 622 A1 | | 9/2015 |
| EP | 0 737 485 A1 | | 10/1996 |
| EP | 1084763 A2 | | 3/2001 |
| EP | 2284822 A1 | | 2/2011 |
| EP | 2626097 A1 | | 8/2013 |
| EP | 2676689 A1 | | 12/2013 |
| EP | 2708254 A1 | | 3/2014 |
| FR | 1196463 | | 11/1959 |
| FR | 2692569 | | 12/1993 |
| GB | 2503028 | | 12/2013 |
| JP | 7-227416 | | 8/1995 |
| JP | 9-299484 | | 11/1997 |
| JP | 7-124230 | | 9/2022 |
| WO | WO 2001/43794 | | 6/2001 |
| WO | WO 2011/111687 | | 9/2011 |
| WO | WO 2020/012127 | | 1/2020 |

OTHER PUBLICATIONS

Nasal Deposition and Clearance in Man: Comparison of a Bidirectional powder device and a traditional liquid spray pump (Year: 2011).*

Binh et al., "Iodine concentration calculated by dual-energy computed tomography (DECT) as a functional parameter to evaluate thyroid metabolism in patients with hyperthyroidism," BMC Medical Imaging, 2017, 17(1):43.

Coda et al., "Pharmacokinetics and Bioavailability of Single-Dose Intranasal Hydromorphone Hydrochloride in Healthy Volunteers," Anesth Analg, 2003, 97:117-123.

Durand et al., Preliminary Study of the Deposition of Aerosol in the Maxillary Sinuses Using a Plastinated Model, J Aerosol Med, 2001, 14(1):83-93.

Haschke et al., "Pharmacokinetics and pharmacodynamics of nasally delivered midazolam," Br J Clin Pharmacol, 2010, 69(6):607-616.

Hollenhorst et al., "Using Intranasal Midazolam Spray to Prevent Claustrophobia Induced by MR Imaging," Am J Roentgenol, 2001, 176(4):865-868.

Kublik et al., "Nasal delivery systems and their effect on deposition and absorption," Adv Drug Deliv Rev, 1998, 29(1-2):157-177.

Lennon et al., "Experiments on Particle Deposition in the Human Upper Respiratory System," Aerosol Science and Technology, 1998, 28:464-474.

Studd et al., "Efficacy and acceptability of intranasal 17 ß-oestradiol for menopausal symptoms: randomized dose-response study," Aerodiol Study Group, Lancet, 1999, 353:1574-1578.

Tschirch et al., "Low-dose intranasal versus oral midazolam for routine body MRI of claustrophobic patients," Eur Radiol, 2007, 17(6):1403-1410.

(56) References Cited

OTHER PUBLICATIONS

Tschirch et al., "Multicenter Trial: Comparison of Two Different Formulations and Application Systems of Low-Dose Nasal Midazolam for Routine Magnetic Resonance Imaging of Claustrophobic Patients," J Magn Reson Imaging, 2008, 28:866-872.
UDS/BDS Product Information Sheet, Aptar Pharma, https://www.aptar.com/wp-content/uploads/2020/07/pds_udsandbds_0-1.pdf, 2016, 4 pp.
Warnken et al., "Personalized Medicine in Nasal Delivery: The Use of Patient-Specific Administration Parameters to Improve Nasal Drug Targeting Using 3D-Printed Nasal Replica Casts," Mol Pharm, 2018, 15(4):1392-1402.
Ylikoski et al., "Bacterial flora in the nasopharynx and nasal cavity of healthy young men," ORL J Oto-rhino-laryngol Relat Spec, 1989, 51(1):50-55 (abstract only).
International Search Report issued on Jul. 30, 2018 in CH 5752018.
International Search Report and Written Opinion issued on Nov. 12, 2019 in PCT/EP2019/061827.
Rudman et al., "Radiographic distribution of drops and sprays within the sinonasal cavities," American Journal of Rhinology & Allergy, Mar.-Apr. 2011, vol. 25, No. 2, pp. 94-97.
Senocak et al., "Sinonasal Distribution of Topically Applied Particles: Computerized Tomographic Detection and the Effects of Topical Decongestion," Otolaryngology-Head and Neck Surgery, vol. 133, No. 6, Dec. 2005, pp. 944-948.
Snidvongs et al., "Does nasal irrigation enter paranasal sinuses in chronic rhinosinusitis?" American Journal of Rhinology, Sep.-Oct. 2008, vol. 22, No. 5, pp. 483-486.
Aggarwal et al., "The assessment of topical nasal drug distribution," Clinical Otolaryngology, 2004, 29, pp. 201-205.
Wormald et al. "A Comparative Study of Three Methods of Nasal Irrigation," The Laryngoscope, 114: Dec. 2004, pp. 2224-2227.
Storey-Bishoff et al., "Deposition of micrometer-sized aerosol particles in infant nasal airway replicas," Journal of Aerosol Science, 39 (2008), pp. 1055-1065.
Cheng, et al., "Diffusional Deposition of Ultrafine Aerosols in a Human Nasal Cast," J. Aerosol Sci., vol. 19, No. 6, pp. 741-751, 1988.
Garcia et al., "Visualization of nasal airflow patterns in a patient affected with atrophic rhinitis using particle image velocimetry," 2007 J. Phys.: Conf. Ser. 85 012032.
Cheng, et al. "Characterization of Nasal Spray Pumps and Deposition Pattern in a Replica of the Human Nasal Airway," Journal of Aerosol Medicine, vol. 14, No. 2, 200, pp. 267-280.
Guo et al., "The Effect of Formulation Variables and Breathing Patterns on the Site of Nasal Deposition in an Anatomically Correct Model," Pharmaceutical Research, vol. 22, No. 11, Nov. 2005, pp. 1871-1878.
Djupesland, "Nasal drug delivery devices: characteristics and performance in a clinical perspective—a review," Drug Deliv. and Transl. Res, (2013) 3:42-62.
Kundoor et al., "Assessment of Nasal Spray Deposition Pattern in a Silicone Human Nose Model Using a Color-Based Method," Pharmaceutical Research, vol. 27, No. 1, Jan. 2010, pp. 30-36.
Extended European Search Report for Application No. 24169154.2 dated Jul. 16, 2024.
Australian Examination Report for Application No. 2024202430 dated Jun. 3, 2024.

* cited by examiner

A	B	C	D	E	F

A          B          C

FIG. 4
FIG. 4a
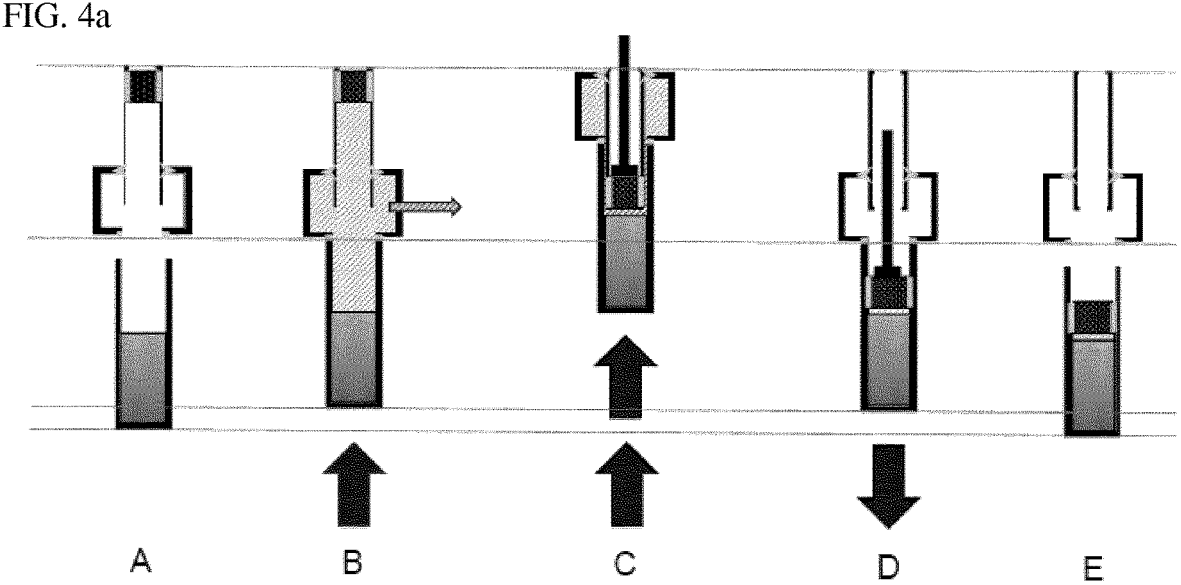
A  B  C  D  E
FIG. 4b
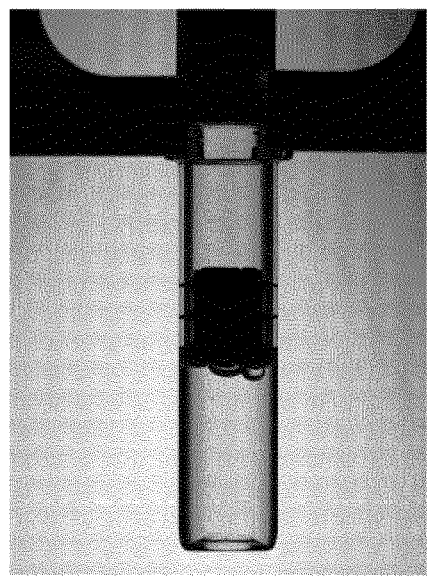

BI-DOSE NASAL SPRAY

CROSS-REFERENCE TO RELATED APPLICATIONS

This application is a national stage filing under 35 U.S.C. 371 of PCT/EP2019/061827 filed May 8, 2019, which International Application was published by the International Bureau in English on Nov. 14, 2019, and application claims priority from Switzerland Patent Application No. 00575/18, filed May 8, 2018, and European Patent Application No. 18209897.0, filed Dec. 3, 2018, which applications are hereby incorporated in their entirety by reference in this application.

The present invention relates to a novel nasal spray containing a solution or a fluid of an active agent with an anxiolytic or anticonvulsant active agent, wherein the nasal spray is characterized in that with the nasal spray, two sprays with each an equivalent, defined volume of the solution or liquid of the active agent, can be intranasally administered to a patient and wherein the nasal spray allows for an administration of the dose, independent of the spatial orientation of the nasal spray in any position of the patient (standing upright, sitting, lying or in any intermediate position). The nasal spray is ready-to-use and can be used directly without prior activation. Preferably it is apparent from the nasal spray whether a spray or even a second spray has been made or effected with the nasal spray. Preferably, a spray of the nasal spray can be administered one-handed by the patient or a third person. The active agent in the inventive nasal spray is preferably an anxiolytic, sedative, muscle-relaxant or anticonvulsant active agent, preferably a benzodiazepine or a GABA receptor agonist such as midazolam or its derivatives or a salt of these active agents (e.g. midazolam HCl). The nasal spray according to the present invention may be used for sedation, premedication or treatment of patients with claustrophobia, anxiety disorders, panic attacks; or for the treatment of convulsions in CNS diseases, particularly epileptic seizures or other manifestations of seizures (e.g. febrile convulsions). The invention also relates to a method for qualitative and quantitative detection of the orientation-independent uniform administration of an active agent in the nasal application and for the detection, by localizing the locally precise nasal deposition of an active agent in the nasal application, as well as a nasal spray, preferably a bi-dose nasal spray, for which it has been shown, using the cited method of detection, that a locally precise and orientation-independent administration of the fluid of the active agent onto the nasal mucosa of a patient can be achieved. The invention also provides a method characterizing and thereby helping to control the patient-specific detection of the locally precise deposition of an active agent in the nasal cavity. Also provided is a method for airless and air-tight sealing of an active agent container in accordance with the invention.

BACKGROUND OF THE INVENTION

Anxiolytic, sedative, muscle-relaxant or anticonvulsant substances that can be used therapeutically are known to the skilled person, such as the fast acting benzodiazepine midazolam (8-chloro-6-(2-fluorophenyl)-1-methyl-4H-imidazole [1,5-a][1,4]-benzodiazepine, including all of its salts). For some time, Midazolam has been used as a drug for anesthetic preparation, sedation, treatment of seizures, sleep induction, and as a sedative or as an anxiolytic (anti-anxiety drug), respectively. There is a substantial risk of tolerance with this drug and it should preferably be prescribed or administered, respectively for a short time only. Midazolam is on the list of essential medicines of the World Health Organization. Midazolam can be applied orally, intravenously, injected into the muscle or by means of a spray into the nose or the mouth.

The administration of midazolam by means of a nasal spray for the treatment of acute cerebral seizures (epileptic seizures) is known. Midazolam in form of nasal sprays is also used for sedation and for preparing patients prior to minor interventions. Midazolam nasal sprays have also been used for some time to comfort patients prior to or during long lasting diagnostic imaging procedures (e.g. magnetic resonance tomography MRT or MRI, positron emission tomography PET, single photon emission computed tomography/computed tomography SPECT, in part computer tomography CT or in combinations of these procedures) and put them at ease [J. Hollenhorst et al.; "Using intranasal midazolam spray to prevent claustrophobia induced by MRI imaging"; *Am. J. Roentgenol.* 176, 865-868 (2001].

For the intranasal administration the therapeutically active agent is sprayed deep into the nose by means of a spray and thus contacted with the nasal mucosa. Depending on the dosage and/or the active agent, a drug administered in this way can act purely locally or systemically. In the case of midazolam a systemic effect is desired. Due to the fact that the nasal cavity is lined by a thin well vascularized mucosa, a drug can quickly get directly into the systemic circulation across a single epithelial cell layer (without a first pass metabolism through the liver or the intestine). In this way, a fast (within a matter of minutes) pharmacologic effect can be achieved.

The intranasal application is especially suitable for strong (potent) drugs for which only a limited amount of an active agent has to be applied onto the nasal mucosa to achieve the therapeutic effect.

A possible disadvantage of intranasal administration is the high variability in the amount of the drug sprayed onto the nasal mucosa and resorbed thereafter. This variability can e.g. be due to an incorrect or heterogenous handling of the nasal spray device [H. Kubik and M. T. Vidgren; "Nasal delivery systems and their effect on deposition and absorption"; *Adv. Drug Deliv. Rev.* 29: 157-177 (1998)]. Problems may also arise if there is a congestion of the upper respiratory tract in the patient or if a larger amount of the sprayed fluid from the nose enters the oral cavity and is then swallowed by the patient. When applied by a healthcare professional, the amount taken up after nasal administration is generally comparable to or higher than after a corresponding oral administration [B. A. Coda, A. C. Rudy, S. M. Archer, and D. P. Wermeling; "Pharmacokinetics and bioavailability of single-dose intranasal hydro-morphine hydrochloride in healthy volunteers"; *Anesth Analg.* 97: 117-123 (2003) or J. Studd, B. Pornel, I. Marton, J. Bringer, C. Varin, Y. Tsouderos, and C. Christiansen; "Efficacy and acceptability of intranasal 17 beta-oestradiol for menopausal symptoms: randomised dose-response study"; Aerodiol Study Group. *Lancet* 353: 1574-1578 (1999), respectively]. All the more important are non-invasive methods without blood collection allowing ad hoc detection by localizing the locally precise application of the administered spray with corresponding resorption.

Several clinical trials concerning the intranasal use of midazolam for anxiolytic pretreatment of MRI patients have already been published.

In a prospective Phase I clinical study with 8 healthy test persons it was found that the mean bioavailability of midazolam after nasal administration is between 76±12% and 92±15%. Formulations administering 1 mg midazolam yielded mean $C_{(max)}$ values between 28.1±9.1 and 30.1±6.6 ng/ml after 9.4±3.2 to 11.3±4.4 minutes. In each case, the absorption of the active agent could be measured already in the first plasma samples [M. Haschke et al.; "Pharmacokinetics and pharmacodynamics of nasally delivered midazolam"; Br. J. Clin. Pharmacol. 69 (6): 607-616 (2010)].

In a multicentric prospective Phase III clinical study [Tschirch F. T. C. et al.; "Multicenter Trial: Comparison of two different formulations and application systems of low-dose nasal midazolam for routine magnetic resonance imaging of claustrophobic patients"; JMRI 28: 866-872 (2008)] two formulations were examined. Patients in the unit dosage group (UDG) received one spray of 0.1 ml of the active agent solution containing 1% (w/v) midazolam and, as a penetration enhancer, 4% of a cyclodextrin derivative (e.g. CAVASOL® W7M Pharma: Manufacturer: Wacker Chemie AG, Munich) from a single-dose nasal spray into one nostril. Patients in the multi dosage group (MDG) received one spray of 0.1 ml of the active agent solution containing 0.5% (w/v) midazolam from a multi-dose nasal spray into each nostril, corresponding to two applications with a total of 1 mg midazolam base as well. Analysis of the results of both groups (in total 108 claustrophobic patients in 4 centers) showed that nasally applied low-dose midazolam is a patient friendly solution to alleviate an MRI examination for claustrophobic patients. The UDG nasal spray was significantly superior to the MDG nasal spray.

In a further study [Tschirch F. T. C. et al.; "Low-dose intranasal versus oral midazolam for routine body MRI of claustrophobic patients"; Eur. Radiol. 17: 1403-1410 (2007)] the efficacy of low-dose intranasally administered midazolam (1 to 2 mg) was compared to orally administered midazolam (7.5 mg) in the treatment of claustrophobic patients prior to routine MRI examinations. In this study (one examination center) 72 patients were randomly assigned to two equally sized groups. In the test group TG1 the patients received 7.5 mg midazolam orally 15 minutes prior to the MRI examination. The patients in the test group TG2 received two, optionally later one to two more sprays from a nasal spray containing 0.5 mg midazolam per spray (in total 1.0 to 2.0 mg midazolam base). In 97% of the cases the MRI examinations could be carried out successfully and without relevant side effects. The MRI imaging quality was significantly higher in patients of the group TG2, compared to the group TG1 (p<0.001). The conclusion was that low-dose intranasal midazolam is an effective and patient friendly solution to avoid anxiety in claustrophobic patients in a broad range of body MRI examinations. In this regard, the anxiolytic effect of nasally administered midazolam was significantly superior to the orally administered form.

Based on these first studies with "low-dose midazolam", midazolam nasal sprays have been used in the clinical practice in the preparation of patients for longer lasting diagnostic imaging procedures (e.g. MRI scans) for quite some time. So far, such midazolam nasal sprays have often been produced in small numbers in hospital pharmacies or public pharmacies with manufacturing permit. However, one cannot optimally adjust the concentration and dose for a nasal application with simple decanting. The challenge in the preparation of the solution is especially the pH dependent recomplexing of the active agent with a solubility shift with each pH change. The thus produced solutions of the active agent are stable in the acidic range only (below a pH of 3.8 and less, depending on the content of the active agent)—at higher pH values the active agent precipitates. In practice, the ideal pH thus must be titrated and stabilized with dilute hydrochloric acid. Thus, an optimal stability for the benzodiazepine ring and its solubility can be achieved. In addition, the solutions should be isotonized to physiological conditions so that the local tolerance on the nasal mucosa is optimal. As these midazolam nasal sprays do not necessarily have to be produced in clean rooms, there is the danger of contamination by germs during production and/or storage. The propagation of germs can be prevented by addition of preservatives such as benzalkonium chloride (usually 0.01% w/v) and/or optionally EDTA (usually 0.1% w/v). However, the addition of preservatives to the solution in the nasal sprays frequently results in irritation of the nasal mucosa. This irritation is often perceived as unpleasant by the patients and can therefore negatively affect the desired sedation of the patient during the diagnostic procedure.

A further disadvantage of extemporaneous nasal spray preparations according to the state of art is a certain batch to batch variability which may lead to differences in the amount of active agent administered. This may be caused, for example, by variations in the spraying device, by incorrect operation of the spray head (pressing sidewards) or an insufficient filling of the spraying tube in a classical nasal spray device. Therefore, with state-of-the-art nasal sprays, it is often difficult to control and make sure how much of the active agent is actually sprayed into the nose of the patient. For proper functioning of the spraying device the patient often must stand or sit upright so that the spraying tube is safely submerged in the solution and does not suck up air. The upright position is easy to achieve in the preparation phase, i.e. shortly before the patient lays down on the MRI table. However, once the patient is laying on the examination table and the table is then inserted into the imaging device for the examination of the patient, an administration in an upright position is virtually impossible. If the patient lying down gets restless during the imaging process, an additional dose administration of the sedative may be severely hampered with the nasal spray of the state of the art or may lead to a situation where the examination has to be stopped, respectively. Respraying twice while lying down is virtually impossible as the spray head does not fill up anymore. If the readministered dose is too low or fails to be applied, the patient remains restless. By contrast, if the dose is too high, the patient may no longer sufficiently react to instructions of the staff during the examination procedure. It is obvious that the patient has to lie as still as possible during the examination procedure and shall only react to instructions of the operating staff (e.g. exhalation and inhalation). If insufficient sedation is achieved, the output quality of the imaging process can be so poor that a repetition of the examination procedure is indicated. As the imaging devices and examination procedures are very expensive and the corresponding instruments need to be well utilized, repetitions of such imaging examination procedures or delays cause unnecessarily high costs which have to be avoided in view of the limited resources in the health-care system. Nor should the increased stress factor of the patient as a consequence of insufficient imaging results or repeated measurements be underestimated. After all, clinical studies have shown that the imaging quality, especially in problematic patients who get restless in the context of such examinations, may be significantly improved by administering low-dose midazolam so that, together with anxiolysis, also better diagnosis will be facilitated thanks to a better image quality.

Typically, a patient will report already on admission or later when entering the MRI examination room that he/she is afraid of the "tube" or the tight examination place, respectively (claustrophobia). Often the patient also comments that he/she has big troubles with the long tubular form of the magnet and its confinement. This may even lead to the patient refusing to have the examination carried out. In addition, coils and further devices required for the examination (e.g. helmets, headsets, breathing belts, pillows, belts, ECG electrodes, caps, posture belts) lead to a corresponding tightness causing further patient problems. Individual patients inherently have more trouble to keep still which is in part disease dependent (e.g. due to Parkinson, dementia or other CNS diseases) or a result of the imminent stress situation which is unique and often completely new for the patient. Many patients also complain about the extremely high noise exposure during an MRI scan and do so, even though often noise protection headphones are being offered or a soothing distraction by music from headphones is tried. All these factors lead to a certain restlessness which may negatively affect the quality of the examination.

After clarifying whether the patient is prone to panic attacks and whether an examination is problematic for medical reasons (e.g. due to respiratory depression, allergies, Myasthenia gravis, or because the patient regularly takes strong CNS acting drugs) the clinician in charge will recommend the use of the nasal spray to the patient and have it provided. After his consent, the patient will receive final information about the examination procedure. The nasal spray according to the state of the art must be administered in a seated position on the examination table. Generally, the nasal spray will first be well filled by spraying 1 to 2 times into the air to secure the filling of the spray tube. Thereafter one spray each will be administered right and left side into the nasal cavity. Often this results in a short irritation that is preannounced to the patient. Every patient reacts differently to it, sometimes even positively, as he clearly feels an effect. As soon as about 1 to 2 minutes after the nasal application the patient does not refuse the MRI examination anymore and easily accepts to be prepared for the examination procedure. Only rarely are further sprays required in this first phase. The patient will now be prepared for the final examination position. The various additional devices such as coils can now also be easily positioned. The patient can then be transferred into the MRI magnet without difficulties by using the position laser for centering. In the affected patients, this is often not possible without premedication. Another major advantage is the "low sedation" effect and therefore the high attention of the patient despite the use of a sleep-inducing drug. The doses used are so low that the patient can very well follow the instructions of the attending technicians without difficulties (conscious sedation). Not only does this facilitate the communication but it also accelerates the examination procedures. Patients who fall asleep during the examination (as it is, for instance, often the case when using higher i.v. doses of the substance midazolam) can no longer follow the instructions and impair the examinations "by breathing", i.e. they cannot hold their breath and cause, by spontaneous breathing, an inferior or even non-diagnostic image quality. By using breathing belts, spontaneous breathing can be reduced but this leads to longer measurement times which is uncomfortable for the patient and should also be avoided for cost reasons.

If, during the examination, the patient once more shows anxiety and/or restlessness, one could administer a further spray with the nasal spray, i.e. the active agent could be redosed. However, due to the lying position of the patient, this is rather limited, since the patient must also be moved from the examination position. In addition, one must try to administer the spray in a lying position in order to keep the position of the patient. Due to the low degree of filling in the nasal spray according to the state of the art this is impeded. If the patient wears a head coil during the examination, a nasal spray according to the state of the art is virtually impossible to use because the space around the nose is too small for orienting the nasal spray into the correct position. In addition, the filling of the spraying device cannot be ensured without an uncontrolled additional burden for the patient.

After completion of the image acquisition, the patient lying on the examination table is retracted from the MR magnet. He can sit up and redress himself. As a precaution measure, many centers do not allow the patients to drive a vehicle themselves after the use of the nasal spray. Understandably, there are almost no data regarding the necessity of these precautions. As partially active metabolites are generated in the degradation of midazolam, one should observe a safety rest of at least 4 hours before driving a vehicle or operating a machine. In this context, it needs to be considered that some patients present a significantly stronger reaction, have a slower metabolization of the active agent or take concomitant medications enhancing the effect.

When using multiple-use nasal sprays there is a risk for some patients that diseases are transmitted from patient to patient. In large examination centers in which a large number of patients are subjected to these diagnostic imaging examinations, special care has to be taken with regard to hygiene. When using multiple-use nasal sprays, the spray head might get in contact with the epithelium of several patients resulting in the transmission of germs if the same head is used for subsequent patients. In the normal bacteriological flora of healthy individuals inter alia *Haemophilus influenzae, Streptococcus pneumoniae, Staphylococcus epidermidis, Staphylococcus aureus* are found. Even though these germs do not necessarily lead to an infection, they can increase the germ load substantially which can be a problem particularly for immunosuppressed patients [Ylikoski J. et al., "Bacterial flora in the nasopharynx and nasal cavity of young healthy men", *ORL Journal Otorhinolaryngol Relat Spec.*, 1989; 51 (1): 50-55]. The spray head needs to be changed for each new patient. However, this is very cumbersome because the staff must be trained accordingly, and each change must be recorded and checked to comply with the hygiene regulations. The change of the spray head also requires a re-control of the pump and its function in order not to erroneously apply a dose of the active agent that is too high or too low.

Further important application possibilities exist in all cases where acute anxiety or panic disorders must be overcome as quickly as possible. The great advantage of the nasal application with its rapid bioavailability of the active agent can be used in an optimal way for the treatment of acute anxiety or panic disorders. The spray allows good anxiolysis and vagal attenuation enabling favorable conditions for all possible interventions. In addition to the MRI examples mentioned the spray has been used successfully in dental interventions, minimally invasive surgical procedures, or with all kinds of invasive interventions. As a premedication, the spray is also suitable for anesthesia preparation or for initiating further anesthetic procedures. Similarly, a successful use in so-called "aggressive" therapeutic procedures (interventions), restlessness, and anxiety as well as in patients who are difficult to approach, in part also in aggressive, restless or disoriented patients is part of the present invention.

The reliable and safe administration of drugs in emergency situations but also the appropriate administration of drugs in situations of spatial limitation is often a great challenge.

Such a situation which requires reliable and fast application of the emergency medication exists inter alia in epileptic or spastic patients who cannot be sufficiently stabilized despite basal anti-epileptic medication and, in case of convulsions, must be rapidly and effectively treated with an anxiolytic or anticonvulsant substance (such as midazolam). Seizures or epileptic fits or seizures may occur totally unpredictably at any time in everyday life. Often the patient lies in an unfavorable position or is difficult to access for a rapid administration of the medication (depending on the setting or position, the movement of the patient impairs the application). The patient himself or the relatives are often confronted with the difficult situation how they should best administer the medicament as quickly as possible. Also, the spasm or the biting fits associated therewith, lead to a stiffening of the patient so that an approach or also, in particular, the oral application of an emergency medication is impossible. The patient often must be moved into a protective position avoiding asphyxiation or the danger of injuring oneself. Priority is the lateral positioning while the upright positioning is virtually impossible. Precious time in emergency treatment can be lost by the repositioning. Therefore position-independent devices are required for administration of the solution of the active agent and of great practical importance in the practice.

Other clinical situations in which the administration is negatively affected rather by extrinsic factors are radiological tomography examinations (MRI, CT, SPECT or PET) or pre-operative interventions (such as tooth interventions, minimally invasive interventions) as well as gastrointestinal endoscopy. The upright position is easy to achieve in the preparation phase, i.e. shortly before the patient is lying down on the examination table. However, once the patient is on the examination table an administration in an upright position is virtually impossible.

Multi-dose sprays according to the state of the art must first be loaded prior to the administration. For this, at least two sprays are triggered for testing purposes (e.g. sprayed into the air) so that a safe and successful administration can take place in an upright position. Furthermore, using traditional multi-dose sprays, it is not possible to repeatedly trigger sprays in a non-upright position. Each time, i.e. after each spray in a non-upright position, it must be repumped. Thus a nasal emergency treatment with the traditional multi-dose sprays is possible only to a very limited extent. Further, the aspiration of air can result in unequal application of volumes, which is undesired.

The intrinsic and extrinsic impairment when administering drugs in the situations mentioned above thus poses a great difficulty for the affected patient, his relatives as well as the intervening nursing staff.

DETAILED DESCRIPTION OF THE INVENTION

The present invention was made in view of the state of the art described above, the aim of the present invention being to provide a nasal spray device with which a defined amount of an anxiolytic, sedative, muscle-relaxing, or anticonvulsant active agent (a benzodiazepine or derivative/GABA receptor agonist such as midazolam or a derivative thereof or its salt, respectively can be intranasally administered and wherein a uniform administration is made possible, irrespective of the spatial orientation of the nasal spray in every position of the patient (e.g. standing upright, sitting, lying, or in any other position or intermediate position of the patient). The nasal spray shall also allow the administration of a second spray with an equal (equivalent) volume of the solution or the fluid of the active agent. That is, the volume of the first and the volume of the second spray are about equal and thus the amount of the active agent dissolved therein, too. In this way, a further equally dosed spray with the active agent can be administered to the patient, once it becomes obvious that the patient is not lying sufficiently still in the examination device.

The solution of this problem is to provide a nasal spray containing an aqueous solution or a fluid with an anxiolytic, sedative, muscle-relaxing, or anticonvulsant active agent and with which two sprays or spray puffs with an equal defined volume each of the aqueous solution or fluid of the active agent can be administered to a patient. The nasal spray is to facilitate a uniform administration irrespective of the spatial orientation of the nasal spray in any position of the patient (standing upright, sitting, lying, or in any intermediate position). The nasal spray can preferably be used directly without prior activation.

The invention thus relates to a nasal spray containing an aqueous solution or a fluid with an anxiolytic, sedative, muscle-relaxing, or anticonvulsant active agent, characterized in that:
  a) with the nasal spray, two sprays or two spray puffs with each an equivalent, defined volume of the aqueous solution or liquid of the active agent can be administered to the patient intranasally;
  b) wherein the nasal spray allows for an equal administration of the dose, independent of the spatial orientation of the nasal spray and in any position of the patient (standing upright, sitting, lying or in any intermediate position).

In the context of the present invention the term spray can interchangeably be replaced by the term puff or the term spray puff (German: Sprühstoss), where appropriate. This does however not relate to the term spray when used in connection with the combined terms e.g. in "nasal spray" because then it refers to a device and not an activity.

In one embodiment, the bi-dose nasal spray consists of the following four components:
  a) a drive element including the spray device referred to as actuator, including a spring and a hollow needle as well as a spraying device;
  b) a vial holder;
  c) an active agent container (e.g. a vial made of glass, metal or a solid plastic);
  d) a tightly sealing plug, preferably a plug made of rubber or a similar material approved for pharmaceutical purposes.

Preferably, the drive element comprises a spring and an injection needle.

In a preferred embodiment, the active agent container contains an anxiolytic, sedative, muscle-relaxing, or antispasmodically acting therapeutic.

In a further embodiment, the triggering of the spray is independent from air pressure by direct shift of the active agent container against the plug by pressure to the drive element, whereby with the nasal spray a spray can be preferably administered directly and without activation. Preferably, it can be identified from the inventive nasal spray device whether the nasal spray is unused or whether one spray or even two sprays have been made.

Using the inventive bi-dose nasal spray, a spray can be administered one-handed by the patient himself/herself or by a third person.

The therapeutic substance in the inventive nasal spray is preferably a benzodiazepine or a GABA receptor agonist such as midazolam or a salt of these active agents.

Thus, the bi-dose nasal spray is particularly suitable for sedation, premedication, treatment of patients with claustrophobia, panic attacks, or anxiety disorders or for the treatment of convulsions in CNS diseases, particularly epileptic seizures or other manifestations of seizures (e.g. febrile convulsions).

Using the bi-dose nasal spray, the active agent can be intranasally administered to a patient, wherein the active agent is injected into or administered onto the nasal mucosa in any conceivable form and is resorbed at this place. The administration should be as uniform as possible and may be done in any position of the patient (e.g. standing, sitting or lying (supine, prone or lateral position)). The orientation of the nasal spray in space is not limiting in this context, which is made possible by the following construction elements:

a) direct shift of the active agent container (glass vial) against the plug by finger pressure;

b) spatially orientation-independent precise control and blocking of the displacement movement;

c) airtight seal of the active agent container containing the active agent filled under reduced pressure with the plug;

d) drive element (also called actuator), consisting of a spring, an hollow needle (riser tube) through which the active agent fluid is pushed up under pressure and is dispensed at the end of the actuator in form of a spray with a spraying device.

In conjunction with the present invention, an airtight seal on the one hand means that the active agent solution is hermetically sealed and that as little as possible or no residual air is left in the active agent container. The active agent container is thus evacuated or airless.

The airtight seal of the filled active agent container (see FIG. 4) and the composition of all four components as described above (a: drive element; b: vial holder; c: active agent container and plug) makes it possible that the inventive nasal spray behaves like a prefilled syringe. Using the inventive nasal spray, one can accordingly administer one dose each of the active agent in every spatial orientation. A blocking system as sketched in FIG. 2 and as defined by the vial holder and the actuator as an active unit, allows a controlled shift of the active agent container with respect to the drive element, and thus allows dispensing exact volumes of the active agent fluid through the hollow needle.

The following describes the preferred embodiment of the bi-dose nasal spray according to present invention. For an easier understanding it is referred to the figures which should not be construed as limiting the invention in any way to the nasal spray devices depicted in these figures.

FIG. 1 shows a schematic view of the composition of the bi-dose nasal spray according to the present invention as well as its major components: the drive element A, also referred to as actuator, the vial holder B, the active agent container C (e.g. a glass vial), and the rubber plug D. On the right is a schematic view of the composition of the four components of the preferred nasal spray device, each with the actuator built in (E) and without actuator (F).

Figure 2:
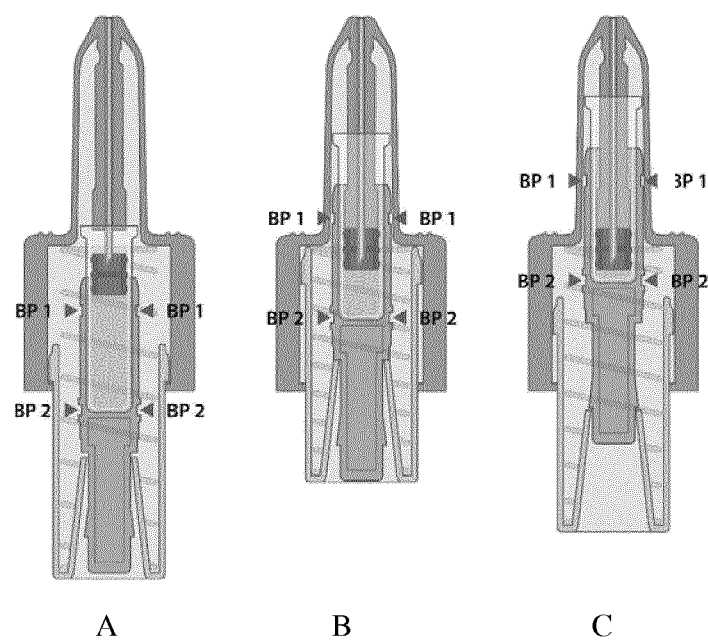

FIG. 2 shows a schematic view of the blocking mechanism of the bi-dose nasal spray. BP denotes the blocking point at which the spraying device is blocked each at the first spray (BP1) or at the second spray (BP2), respectively. FIG. 2A shows the bi-dose nasal spray in the starting position (BP1 and BP2 as the lowest position). In FIG. 2B it can be seen how the actuator is compressed at the first mechanical pressure from the bottom. The hollow needle perforates the plug and the glass vial shifts to the rubber plug so that the fluid is pushed out through the hollow needle of the actuator and the first spray is triggered. The vial holder thereby shifts into the first position in which the blocking mechanism for the first spray between the actuator and the vial holder is secured by the small anchor in BP1. Thus it is not possible for two doses to be delivered in a single spray puff. In FIG. 2C the same mechanism as in FIG. 2B follows by pressure from below. The residual volume is sprayed but with the difference that the plug is now fully at the bottom of the glass vial and the vial holder is now in the highest position. This ensures the dual dosage of the spray, besides no further spray is possible. In addition, the user notes that the nose spray is now empty, since there is no back pressure after the application and the lower part is fully shifted to the top.

Figure 3:
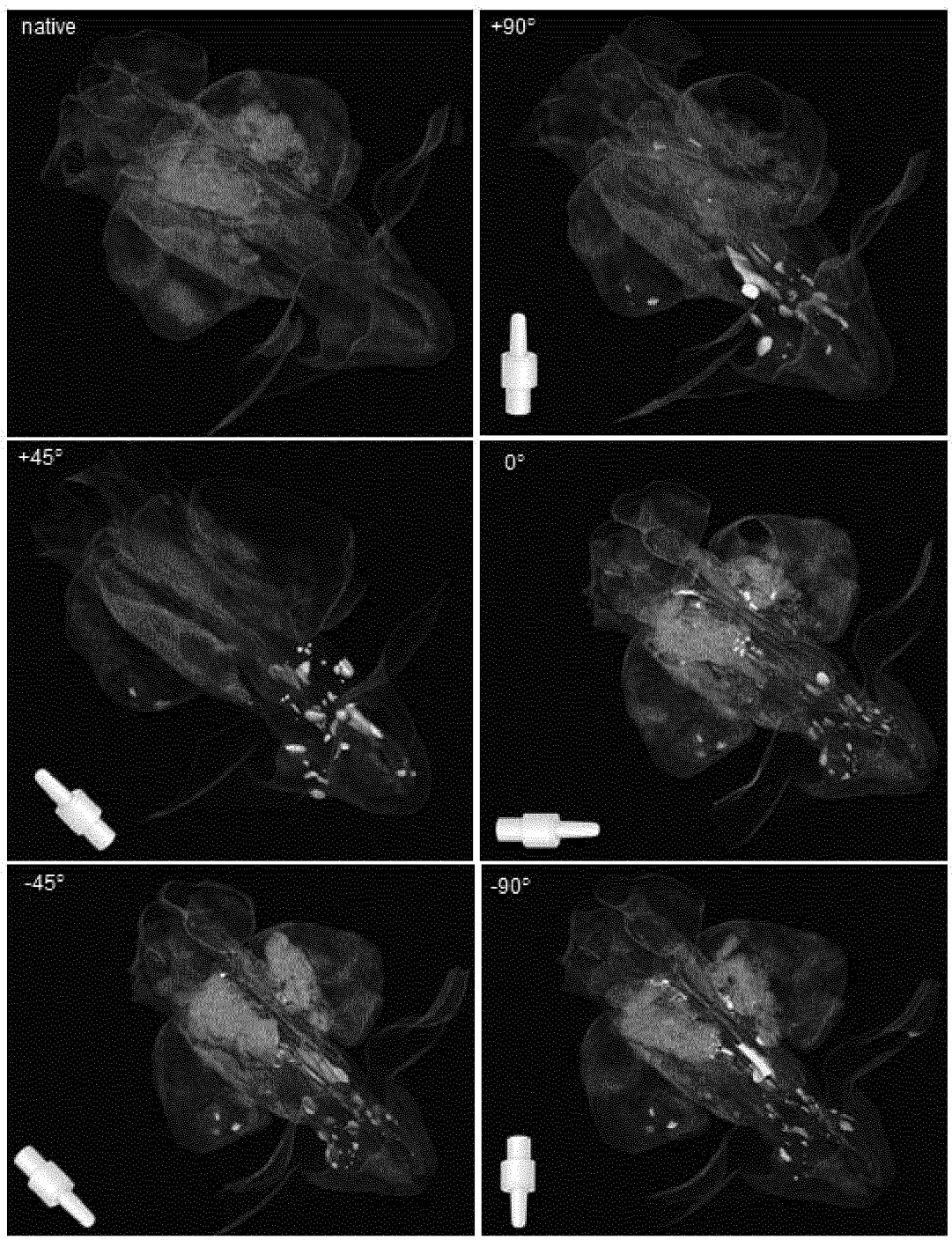

FIG. 3 provides a depiction of the precise deposition locally of the solution of the active agent after application with the nasal spray of the invention, depending on the orientation of the nasal spray in space. The top left image shows the CT image before the application. The subsequent images show the CT image after the application, wherein each of the images depicts the orientation of the nasal spray in space and does so by means of a schematic view of the nasal spray showing in which position the administration is made (top right image—straight up; middle right image—horizontally; bottom right image—straight down). The remaining images show the administration in intermediate positions. The application angle between the nasal spray and the nose is constant in these cases. The high contrast active agent solution appears bright and is clearly visualized.

FIG. 4 shows in FIG. 4a a schematic view of the preferred method for an airtight sealing of the active agent container. The active agent solution is filled into the active agent container under atmospheric pressure. Preferably, the filling is immediately prior to the sealing procedure as shown in FIG. 4. The bottom part of FIG. 4a A shows the active agent container which is open at the top with the filled-in active agent solution (grey), and in the upper part the sealing chamber positioned above with the cylinder and the plug inserted therein at the upper end. This step is done under atmospheric pressure in the whole system. The arrow-shaped grey triangles depict sealing gaskets on the sealing chamber, and the grey rectangles at the plug show zones in which an airtight closure is enabled by the lips of the plug.

FIG. 4a B shows the active agent container which has been pushed against the sealing chamber. Thus an airtight unit is formed. Through a lateral outlet, the air in the closed system is aspirated (see arrow symbol). This is done in a time-controlled fashion and under controlled aspiration power. The area with negative pressure in the closed system is shown shaded. The light grey areas show the sealing points. The thick arrow under the active agent container points into the direction in which the active agent container is pushed against the seals.

In FIG. 4a C the whole system (active agent container and sealing chamber) is pushed upwards so that the cylinder in the active agent container will be placed at its defined position (first large arrow). Immediately thereafter the piston lowers the plug to the surface of the active agent solution, and the plug is fixed close to the glass vial by the expansion of the lips of the rubber plug (see second large arrow). This step is done with negative pressure (constant aspiration of the air). The shaded area shows the area with negative pressure. By this step the plug is fixed close to the surface of the active agent solution.

FIG. 4a D shows how the closed active agent container and the sealing chamber are pushed downwards (large black arrow), thus repulling the cylinder (without the plug) out of the active agent container. The area above the plug is now again under atmospheric pressure (aspiration of air was stopped). The plug is now fixed just above the active agent solution in the active agent container (shown by grey vertical stripes at the side of the plug). Should a gap be formed between the plug and the active agent solution, there would be negative pressure at this place.

FIG. 4a E shows how the sealed active agent container was lowered back to the original position and separated from the sealing chamber. The closed active agent container can now be assembled to an inventive nasal spray. The sealing chamber can be reused for hermetic sealing of a new active agent container with a plug. The person skilled in the art knows how to automate the method described in FIG. 4.

FIG. 4b shows an already filled hermetically sealed active agent container. The image shows that the rubber plug hermetically seals the active agent solution and that only minimal residual air is left between the plug and the active agent solution.

Figure 5:
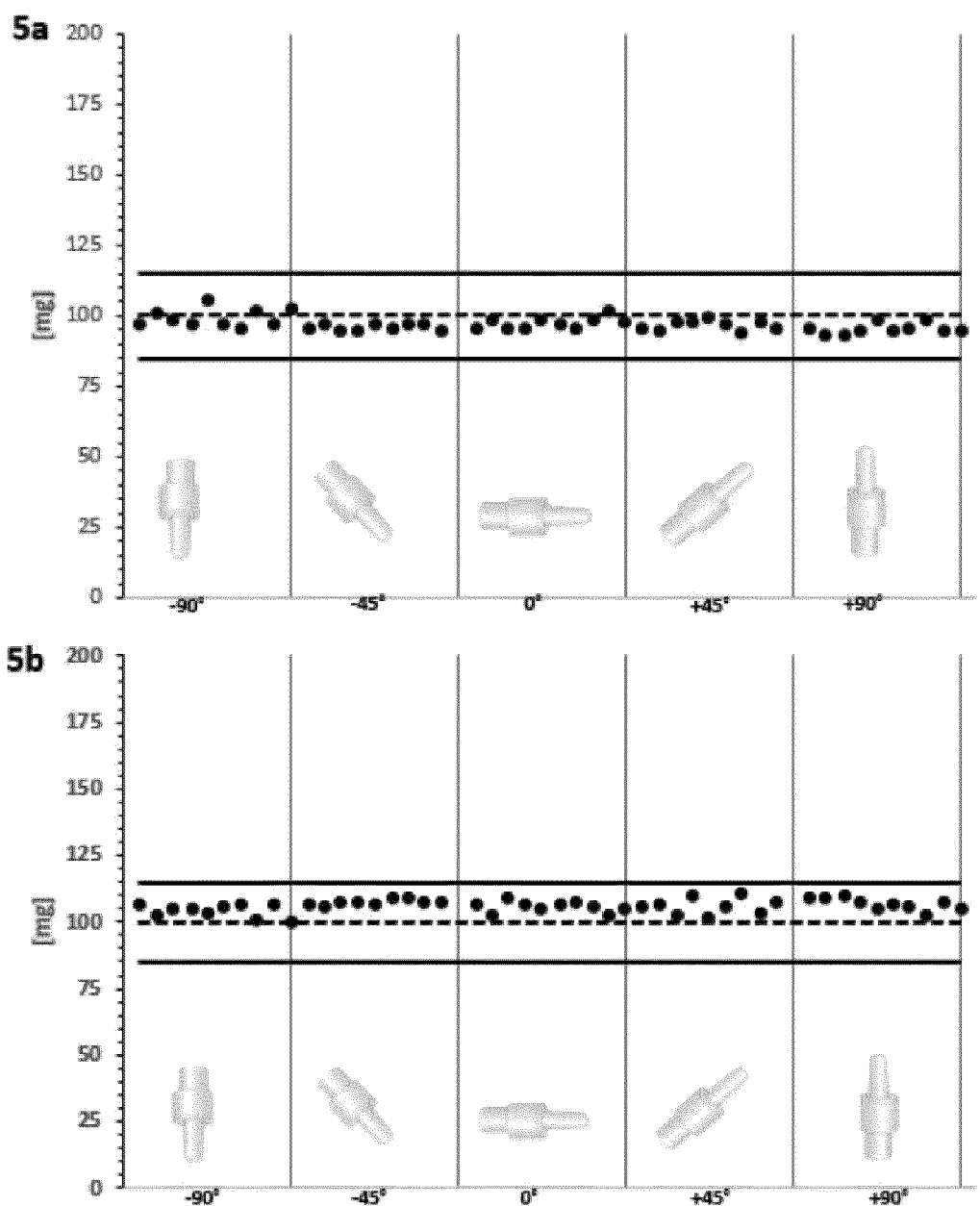

FIG. 5 shows the uniformity of mass of the two sprays (in mg active substance applied to the nasal mucosa), depending on the orientation of the nasal spray. FIG. 5a shows the series of measurements for the first spray and FIG. 5b shows the series of measurements for the second spray. Shown are 10 measuring points each (one nasal spray each per measurement) per orientation of the nasal spray. The dashed line shows the target value (100 µl per spray) and the solid lines show the acceptance criteria of 15% (85 mg-115 mg) required according to US American Pharmacopoeias which are the most strict for pharmaceutical production compliance.

In the bi-dose nasal spray according to FIG. 2 the shift of the vial holder with respect to the lower edge of the actuator should be noted. This is visible when the operator looks at the bi-dose nasal spray from below. This enables the patient, the nursing staff, or the physician to determine whether still two, one or no dose at all can be administered with the nasal spray. A prior use, i.e. an opening of the spraying device is thus clearly visible. Preferably, the spraying device in the nasal spray of the present invention is blocked after the second dose, and therefore no further dose can be administered. This increases the safety and avoids improper use compared to multi-dose sprays.

Preferably, the inventive nasal spray contains 200 to 230 µl, 215±15 µl, 230±10 µl, 225±10 µl, or 225±5 µl of the solution, the fluid or the powder of the active agent. With each spray of the bi-dose nasal spray according to present invention one can apply a volume of 75, 80, 90, 100, 110, 120, 125, 130, 140, or 150 µl (with a volume range of ±25% each) of the aqueous solution of the active agent or the fluid of the active agent, wherein in a particularly preferred embodiment, with each spray, one may spray a volume of 100±15 µl, 100±10 µl, preferably 100±5 µl of the fluid with the active agent onto the nasal mucosa. To this end, the nasal spray is filled with 200 to 300 µl of the aqueous solution or fluid of the active agent, wherein, in a particularly preferred embodiment, the nasal spray is filled with 230±10 µl of a fluid containing the active agent (advantageously as a solution).

The iso-osmolar aqueous fluid with the active agent is dosed in such a way that with each spray, depending on the intended application, a therapeutic dose of 0.25 to 5 mg or of 1.0 to 10 mg of the active agent (for example, midazolam, a derivative thereof, or a salt of these active agents) can be administered. The active agent fluid (preferably an aqueous fluid) with the therapeutic active agent may additionally contain a preservative such as benzalkoniumchloride in a concentration of 0.01% w/v and EDTA in a concentration of 0.1% (w/v). Further approved preservatives or additives for fluid pharmaceutical formulations that can be used in the nasal sprays of the present invention are well known to the person skilled in the art and described in relevant textbooks. Depending on the concentration, the aqueous fluid with the active agent midazolam has an adjusted, precisely defined pH value, preferably with a pH value between 2.8 to 3.8 (preferably a pH value between 3.0 to 3.5). Depending on the specification, these limits can be selected with a narrower tolerance or optionally adjusted by the person skilled in the art. Possible additional additives are ones that help to adjust the osmolality (e.g. salts, glucose), solubilizers (e.g. cyclodextrins), penetration enhancers (which cause an improved uptake of the active agent across the nasal mucosa, e.g. dextrins, cyclodextrin, chitosan or derivates thereof), wetting agents (e.g. glycerol, propylenglycol) or chelators such as EDTA or DTPA. For anhydrous sprays, midazolam has to be either dissolved by means of solubilizers or has to be suspended. It may then not be possible to maintain the above-mentioned pH values as well as the iso-osmolality. Powdery nasal sprays in form of mixtures of the active agent based on micronized midazolam, possibly mixed with various carrier substances such as cyclodextrins may be used.

In a preferred embodiment, the bi-dose nasal spray does not contain preservatives, i.e. the fluid formulation in the nasal spray only contains midazolam HCl in an aqueous iso-osmolar NaCl solution. Preferably, such a formulation is aseptically prepared so that the corresponding bi-dose nasal spray can be stored over a longer time (preferably more than 10 months, more preferably 12 months, even more preferably 18 months, or most preferably 24 to 36 months), without a loss in quality. The advantage of this nasal spray formulation without preservatives is a lower allergisation, irritation and interaction with the movement of ciliae on the nasal mucosa.

As schematically shown in FIG. 4a, the active agent container is preferably filled with the active agent solution and sealed. First, the desired amount of active agent is filled into the active agent container which is open at the top. Then the active agent container is introduced into a sealing chamber containing a plungerlike device. At the lower end of the plungerlike device a plug is fixed with which the active agent container is to be hermetically sealed. The sealing chamber and the active agent container now form a closed system. Through an opening at the side of the sealing chamber air is aspirated into the closed system, whereby the active agent in the container is to remain unchanged. By validation experiments it has been determined that a negative pressure of about 600 to 900 mbar is to be used in order to place the plug as close as possible to the surface of the active agent solution. Experimentally, a preferred aspiration time of 0.5 to 1.5 seconds has been determined in order to achieve the desired negative pressure in the system. By means of the plungerlike device, the rubber plug is lowered into the active agent container to the upper level of the active agent so that, as far as possible, no gap is formed between the surface of the active agent filling and the plug. Thus the sealed filled active agent container behaves like a filled syringe, and the active agent fluid of the inventive nasal spray thus can be applied in every spatial orientation. The orientation independent application of two equal sprays was tested by a person skilled in the art with several samples, and the conformity of these was documented according to common pharmaceutical requirements (FDA, PHEUR) (two uniform sprays with a volume of 100 μl±15% each, see FIG. 5).

The applied vacuum with which the negative pressure in the system is created (see FIG. 4B) can preferably be constantly monitored and recorded. The desired negative pressure in the closed system is preferably controlled by the aspiration time. By validating experiments it has been found that an aspiration time of about 1 second is generally sufficient to place the plug in the active agent container in such a way that, as far as possible, no residual air or only a minimal amount of residual air remains between the plug and the surface of the active agent fluid (compare FIG. 4b).

As can be seen from FIG. 5, the method described above for the airtight sealing of an active agent container allows its incorporation into a nasal spray according to the present invention. This facilitates the production of a nasal spray for administration of two sprays with an equal defined amount of the active agent or an equivalent volume of the active agent solution, wherein the nasal spray allows a uniform administration of the active agent irrespective of the spatial orientation of the nasal spray and in any position of the patient (standing upright, lying or in every intermediate position). The resulting nasal spray meets the requirements of the Pharmacopoeias of the regulatory authorities (e.g. in the USA).

The above-described method for airtight sealing of active agent containers is suited for industrial scale use, in particular since the space in which a negative pressure has to be created, is very small and because the aspiration time is only about 1 second.

Preferably, a visual inspection is done with each sealed filled active agent container. The visual control can be performed by means of a camera (optionally computer-controlled). The distance between the plug and the surface of the active agent fluid is controlled. By means of validation experiments a person skilled in the art can define acceptance criteria for the maximum permissible distance. This allows for an automated sorting of improperly sealed and/or incorrectly filled active agent containers.

The inventive nasal spray works as described in the following. By exerting finger pressure on the drive element (actuator) there is a displacement of the plug into the active agent container, thereby creating a pressure that causes the active agent fluid to be pushed up through the hollow needle built into the drive element into the upper spiral part of the actuator and to be dispensed as a spray (see FIG. 2). The blocking mechanism between the vial holder and the actuator (compare legend to FIG. 2) allows the delivery of two controlled sprays with an equal volume each.

Preferred is a bi-dose nasal spray with which two controlled sprays of 0.2 to 5 mg each, particularly preferred 0.278-5.56 mg midazolam HCl can be successively administered to a patient in an isotonic aqueous solution, whereby it does not matter whether the nasal spray is held in an upright, a horizontal or an upside down or in any intermediate position. The two sprays may be performed in rapid succession or in a timely manner, whereby it is preferred that the second spray is to be made into the other nostril. The bi-dose nasal spray allows a distribution of the active agent over a large area onto the surface of the nasal mucosa which proves to be advantageous in view of a rapid resorption and bioavailability.

In a particularly preferred embodiment the nasal spray can be used directly without any further preparation or activation for administering the active agent, i.e. it is an off-the-shelf ("ready-to-use") bi-dose nasal spray.

As mentioned above, the bi-dose nasal spray consists of four prefabricated main components. These four main components may be sterilized (steam, ethylene oxide and/or gamma sterilisation). The bi-dose nasal spray is then assembled from these four main components, the active agent container also being filled with the active agent fluid in order to obtain the desired bi-dose nasal spray according to present invention.

The filling of the active agent container, preferably a glass vial, is done in a closed environment by means of a needle and a precision metering pump with which the desired volume of the active agent solution (e.g. 200 to 300 μl) can be filled into the active agent container in precise doses. The degree of filling of each active agent container is controlled and photographically documented. For this purpose, the light intensities of the diffracted light beams at the glas boundaries below and above the plug are measured and compared; hence the degree of filling in the active agent container is thereby precisely controlled.

With the bi-dose nasal spray according to FIG. 2 only two successive sprays can be administered. When pressed for the first time, the upper rubber seal is pierced and shifted up to special point (BP1/BP2 as well as the inner shaft). The dispensed quantity of active agent fluid (spray volume) is controlled via lateral anchors (see BP1 and BP2 according to FIG. 2). By virtue of a spring the spray is "reactivated" and can then be activated a second time (FIG. 2, bottom middle image). The maximum volume that can still be dispensed is determined by the residual volume which in turn is defined by the maximal stop in the upper narrower nose cylinder (FIG. 2, bottom right image). The lateral shafts with the points BP1 and BP2 additionally control the position and thus the precise application in two phases. By means of the lateral anchors a two phase application results. The bi-dose nasal spray is designed in such a way that the spraying mechanism is blocked and depleted after delivery of the second spray. Hence, the bi-dose nasal spray can no longer be used. In practice, it will be safely disposed according to the regulatory requirements.

The bi-dose nasal spray according to the present invention will be packaged after production, preferably in a box made of cardboard or plastic, wherein one box may contain one or several metered-dose sprays and each contains a package insert describing the use of the inventive nasal spray. For storage and distribution multiple boxes can be packaged in further boxes (large packages). In an emergency case, this enables a parallel application of the emergency medicine via both nostrils without further delay.

Before the bi-dose nasal spray according to the present invention is delivered to the end customer, a quality control is done to verify the density, pH, osmolality of the formulation as well as the active agent by HPLC (validated procedure similar to PH. Eur.). In addition, a microbiological analysis is done for each batch. As described above, the filling quantity in the active agent container is controlled during the filling process. In each production batch, the uniformity of the dosage in the bi-dose nasal spray must be controlled according to the Pharmacopoeia in a verifiable way.

In the bi-dose nasal spray according to the present invention the expelled fluid is not replaced by air as in the commonly used nasal sprays, instead a movable plunger is used which is pierced when the spray mechanism is activated. This system allows an intranasal administration of the spray irrespective of the spatial orientation of the nasal spray in any position of the patient (i.e. standing upright, sitting, lying or in every other position of the patient). This significantly differentiates the bi-dose nasal spray according to the present invention from the nasal sprays according to the state of the art such as customary multi-dose nasal sprays.

The closed system facilitates the microbiological integrity of the primary medicine container from the time of the aseptic production to the time of use of the nasal spray. The aseptic filling of the bi-dose nasal spray according to the present invention allows to avoid the use of a possibly irritating preservative in the formulation of the pharmaceutical substance. The bi-dose nasal spray according to the present invention is stable upon storage.

The bi-dose nasal spray according to the present invention is an immediately ready-to-use device that can be operated one-handed, if necessary by the patient himself (herself). The bi-dose nasal spray according to the present invention is suitable and applicable for diagnostic imaging procedures such as MRI scans and does not affect the diagnostic device and its function or integrity is not affected by the diagnostic device (e.g. by the magnetic radiation of the device or its magnetic forces). It also does not cause magnetic interference or other artifacts in the imaging procedure.

The bi-dose nasal spray according to the present invention optionally also allows an oral application. This can be done if the nose is blocked (e.g. by local pathological changes) or if a local application is limited in case of a cold or common infections concerning the nasal pathways. Possible contraindications are e.g. recent rhinoplasties, polyps, or other acute inflammations in the nasal cavities.

The bi-dose nasal spray according to the present invention is particularly suited for various indications, e.g. claustrophobia or a similar anxiety disorder with or without restlessness before entry or positioning for the MRI or similar machine (PET, SPECT, radiation therapy equipment or also CT). A claustrophobic patient is sedated already about 1 to 2 minutes after intranasal administration of one or two sprays from the bi-dose nasal spray so that a successful MRI examination is possible without any problems.

Moreover, using the bi-dose nasal spray according to the present invention, various similar fears, such as of minimally invasive interventions, of dental interventions, pediatric interventions, various diagnostic procedures, in palliative steps prior to gastrointestinal examinations can be overcome or reduced. Further uses include the premedication prior to anesthetic procedures, surgical interventions, or similar procedures. Due to the ready-to-use device, the bi-dose nasal spray can be used immediately and independent of the spatial orientation of the nasal spray in every position of the patient. Thus the bi-dose nasal spray can be used very effectively also in cases of emergency or particularly in the above-mentioned interventions. Further applications concern the use in geriatrics as well as rather bothering therapeutic interventions, in cases of anxiety or restlessness as well as in difficult, hardly approachable restless patients.

The low-dose midazolam commonly used with anxiety disorders (preferably 0.25 to 5.0 mg) does not lead to a noticeable sedation of the patient ("conscious sedation"). The patient can therefore follow the instructions of the technicians in charge or the medical assistants who conduct the examination.

The sprays with a bi-dose nasal spray can be administered to the patient by a physician or a medical assistant or optionally also by a nurse or technician present at the examination or intervention. This has the advantage of a rapid intervention also with difficult patients or in cases of compliance deficits, independent of the position of the patient. Using the bi-dose nasal spray, the patient can optionally also administer the intranasal spray to himself (herself).

In a further embodiment of the invention, if necessary, an additional spray with the bi-dose nasal spray according to the present invention is administered to the patient during MRI or a similar (radiological) examination or the mentioned interventions or, as mentioned above, it can be administered by the patient himself (herself) so that the position of the patient during the examination or the intervention is not altered. This is extremely important during a MRI examination with varying contrasts (T1, T2, diffusion, ADC, dynamic, native and with gadolinium as contrast agent) and the requirement that the patient may not move. By this, the redosing is significantly simplified and a misapplication is avoided.

The present invention therefore also relates to a method for treatment of patients in the context of MRI or a similar (radiological) examination, characterized in that a spray with a bi-dose nasal spray according to the present invention is administered to the patient immediately prior to the MRI examination or that he (she) readministers it in the MRI device (e.g. with recurring anxiety or restlessness during the examination).

Anticonvulsant agents in higher dosage are also suitable for the treatment of seizures in patients. Such seizures (e.g. myoclonic seizures) may be caused by various fits such as epileptic disorders or other neurological diseases or with CNS crises as well as with febrile convulsions.

The inventive bi-dose nasal spray can therefore also contain a higher dose solution or fluid of the active agent. The groups of patients who profit from such a high dose nasal spray are typically children, adolescents, young adults or other patients with tonic-clonic epilepsy-like spasms or seizures and convulsions up to febrile seizures. The paroxysmal epileptic seizures or similar CNS seizures develop all of a sudden, often without clear signs and with a certain depressed level of consciousness that sometimes may last for a short time only. Affected persons respond to their surrounding in a limited way only, respond with movements of the mouth or the head, scream all of a sudden, cannot remember later on, fall or writhe, overstretch head and neck, cramp, involuntarily bite their tongue or cheek and often develop a foam-like saliva out of the mouth. The skin of the patients turns slightly blue as a result of a low-grade hypoxia. The muscle tone of the affected muscles may loosen all of a sudden so that affected persons fall or their legs buckle. Occasionally, the seizures last very long and are dangerous. In addition, areas in the central nervous system (CNS) may be destroyed in such seizures. Depending on the affected area of the brain, the symptoms are very different. In affected patients who have already experienced such seizures, early signs may be partly detectable, such as dysphoria, irritability, headaches, certain sensory disorders, noises, hallucinations or a certain aura. This allows the early use of the midazolam nasal spray for taking the edge of the seizure. In this way, the spastic tonic-clonic seizure can also be reduced and/or shortened at best. Midazolam can also be administered orally (tablets) or rectally but these dosage forms have the distinct disadvantage that the active agent cannot act immediately.

The recently introduced orally administered midazolam solutions have the disadvantage that the active agent is resorbed in a delayed fashion (30 to 60 minutes, depending on the degree of filling of the stomach and/or the duodenum). After the resorption, a first liver passage takes place via the portal vein which in turn leads to reduced efficacy due to the first pass effect. Using a nasal spray, the active agent can be brought into the blood much more rapidly and with a much higher bioavailability (about 80%) since the first pass effect can be avoided by nasal administration.

Using the bi-dose nasal spray according to the present invention the anticonvulsant substance can be rapidly, safely and easily directly administered by relatives or third persons without prior activation, especially with epileptics, e.g. with spasmodic bite attacks. As mentioned already, due to the rapid bioavailability, the rapid action, and the simple application with no first pass effect, the nasal application using the nasal spray according to the present invention is significantly superior to the oral or rectal administration. This offers great advantages for the relatives or other caregivers who look after the patients or even treat them in case of emergency. When using a multi-dose nasal spray the head of the patient must be in an upright position. To achieve this, the relatives are forced to somehow hold the patient in a sitting or upright position so that a nasal administration gets possible. This is not necessary with the bi-dose nasal spray according to the present invention since an administration is ad hoc possible, irrespective of the spatial orientation of the nasal spray in every position of the patient. Thus the bi-dose nasal spray according to the present invention is especially suitable for emergencies because a rapid deterioration of the seizure can be stopped early therewith.

In this context it should be noted that sometimes the administration of a single dose may not be sufficient, as the dose response depends on the body weight of the patient (a sufficient dose of the active agent in case of seizures is often about 0.02 to 0.05 mg/kg body weight). Sometimes the administration of a second dose may be required. Using the bi-dose nasal spray according to the present invention a second spray with a second dose of the active agent can be administered immediately or in a time-shifted fashion. This is an advantage compared to other customary products such as Nazolam® (MEDIR B.V., Doom, Netherlands).

Typically, higher doses of the active agent midazolam (1-10 mg) are applied intranasally when a patient suffers from any type of CNS crisis, seizures (e.g. febrile seizures), epileptic disorders and/or seizures associated therewith. Treatment with higher doses may be indicated with early stages of seizures or with symptoms of similar CNS disorders. The nasal spray according to the present invention can be administered by the patient himself (herself) in every position (ready-to-use) or by a third person involved in the emergency treatment. The intranasal uptake is quick and the soothing effect has a very rapid onset.

The measurement of the bioavailability of the active agent after administration of midazolam using the bi-dose nasal spray according to the present invention shows that high bioavailability is achieved (>83%). Since there is no first pass effect with resorption via the nose capillaries, a significant plasma concentration is achieved already 2 minutes after administration. Peak levels of the plasma concentration were measured 5 to 10 minutes after the administration (however, high standard deviations were revealed). This proves that the local uptake of the active agent is very rapid. The half-time of excretion (t1/2β) corresponds to 1.5 to 3.5 hours.

Administration of midazolam by means of nasal spray can lead to a local irritation in the nasal mucosa. However, this usually disappears already 10 to 20 seconds after the administration. The reason for this reversible irritation is probably the low pH of the fluid in the nasal spray (preferably pH 3.0 to 3.5). Possibly, the irritation of the nasal mucosa may also be caused by or partly caused by preservatives that are possibly present. This can be reduced by means of penetration enhancers as an additive (dextrins and derivatives, chitosan and derivatives), with moisturizing agents (propylene glycol, glycerol) or even with chelators (EDTA, DTPA).

When administering midazolam using a bi-dose nasal spray in accordance with the present invention, the known usual precautions have to be taken in order to avoid undesirable side effects. For example, a higher dosage can lead to dyspnoea or respiratory failure. However, the reported cases are extremely rare (1 case has been reported in the last 12 years). Myasthenia gravis may also be enhanced by the administration of midazolam. There are also reports about contradictory or paradoxical effects in children. Generally, similar undesirable adverse events can occur especially in older patients.

The person skilled in the art knows how to produce or provide a drive element as it is mentioned above. The additional components can be purchased. The person skilled in the art can easily assemble the components to a finished nasal spray. The vial holder usually consists of synthetic material or plastic. It serves to take up the container with the active agent (mostly prefilled). The plug serves to facilitate an airtight connection between the drive element and the active agent container. The rubber plug preferably consists of a rubber suitable for the pharmaceutical practice but may also consist of other corresponding plastic materials known to the skilled in the art.

The construction design of the nasal spray is depicted in FIG. 1 and FIG. 2. The nasal spray according to FIG. 1 is built in such a way that a direct displacement of the active agent container (preferably a glass vial) against the rubber plug can be done by pressing with a finger, thereby allowing an air pressure independent triggering of the spray. The nasal spray device according to FIG. 1 allows an orientation independent precise control and a blockade of the shifting movement (FIG. 2) and thereby determines the integrating volume controlling functionality of the actuator (FIG. 2).

Preferably, the nasal spray according to the present invention is characterized in that it can be identified whether the nasal spray is still unused.

The nasal spray according to the present invention is characterized in that the shift of the vial holder against the lower edge of the actuator from the bottom side is visible and thus also whether the nasal spray has already been used or if one or already two sprays have been triggered. Preferably, the nasal spray according to the present invention is characterized in that the assembled nasal spray contains a blocking mechanism that ensures that a first spray is delivered in a controlled way without also triggering the second spray at the same time (compare FIG. 2).

Preferably, one or two sprays can be administered with the nasal spray according to the present invention without the nasal spray having to be activated in advance.

This way, the sprays can be directly administered to the patient or by the patient, one-handed and without preparatory actions. In this case, the volume of each spray is selected in such a way that the aqueous fluid is injected or sprayed, respectively, onto the nasal mucosa and can be resorbed therefrom.

Using the nasal spray according to the present invention, a dose of 0.25 to 5 mg of the anxiolytic, sedative, muscle-relaxing, or anticonvulsant active agent can be administered to achieve a conscious sedation.

Using the nasal spray according to the present invention a dose of 1 to 10 mg of the anxiolytic, sedative, muscle-relaxing, or anticonvulsant active agent can be administered to achieve a spasmolytic effect.

The herein preferred active agent solution in the nasal spray according to the present invention can additionally contain a preservative, e.g. benzalkonium chloride in a concentration of 0.01% w/v and EDTA in a concentration of 0.1% (w/v). However, one can also use preservative-free nasal sprays, in particular in allergy sufferers or when there is a known hypersensitivity.

The preferred active agent solution in the nasal spray according to the present invention has a pH value between 2.8 to 3.8; preferably a pH value of 3.0 to 3.5. The anhydrous fluids or powders as well do not have a measurable pH.

The preferred active agent solution in the nasal spray according to the present invention is iso-osmolar.

The nasal spray according to the present invention is preferably prepared aseptically.

The nasal spray according to the present invention preferably does not cause magnetic interference.

The nasal spray according to the present invention is suitable for treatment of patients with claustrophobia or anxiety disorders, whereby with each spray 0.56 mg midazolam HCl are administered per spray (corresponds to 0.50 mg midazolam base).

The nasal spray according to the present invention is suitable for sedation or premedication, whereby with each spray e.g. 0.278 to 5.56 mg midazolam HCl are administered per spray (corresponds to 0.25 to 5 mg midazolam base).

The nasal spray according to the present invention is suitable for the treatment of patients with claustrophobia or anxiety disorders or for the treatment of patients with an epileptic seizure or other seizures, respectively, whereby, as described above, a higher dose of the active agent of e.g. 1 to 10 mg midazolam per spray or 0.02 mg to 0.5 mg midazolam per kg body weight of the patient per spray is needed with such a treatment.

On one hand, the nasal spray according to the present invention is used for the treatment of patients in the context of MRI or a similar (radiologic, radiation therapy) examination (or further imaging machines in form of a tube or similar), whereby a spray with the nasal spray according to the present invention is administered to the patient shortly before the MRI examination. If necessary, a further spray from the nasal spray according to the present invention can be administered to the patient before or during the examination.

On the other hand, the nasal spray according to the present invention is used for the treatment of patients with a neurologically caused seizure, whereby a spray with the nasal spray according to the present invention is administered to the patient, whereby, if necessary, another spray from the nasal spray according to the present invention can be administered to the patient.

Thus the advantages of the bi-dose nasal spray according to the present invention are as follows:

A rapid specific anxiolytic effect during the preparation phase on the MRI table as well as in similar diagnostic examinations (PET, SPECT, CT) or in all sorts of minimally invasive interventions (dentist, surgery, anesthetic induction) accelerates the work flow and facilitates the planned interventions in the patient.

The administration of low-dose midazolam leads to an improved cooperation with the technical staff during a MRI examination (conscious sedation) or the various minimally invasive interventions.

Enhancement of the imaging quality with fewer motion artifacts (MRI) and better compliance in the above-mentioned interventions.

Lower CNS or systemic toxicity due to a lower peak concentration of the active agent midazolam.

Temporary sedation.

Administration of the active agent is well controllable and possible via two nostrils.

The bi-dose nasal spray can be used with uniform efficiency in lying, sitting, upright position or in any other position of the patient, e.g. also in lateral position. The spatial orientation of the nasal spray is not limiting in this case.

The bi-dose nasal spray is supplied ready-to-use and can be immediately used.

A bi-dose nasal spray is used in one patient only and therefore meets high hygienic standards.

As the formulation in the bi-dose nasal spray can be aseptically filled into a closed system, no preservatives need to be used.

In emergencies with an obstructed nose or local limitations, the nasal spray can be sprayed quickly, efficiently and without any preparation directly into the mouth.

The bi-dose nasal spray meets regulatory requirements, e.g. for registration at Swissmedic, EMA and/or FDA.

By means of the nasal sprays, various midazolam formulations such as anhydrous solutions, suspensions or even powders can be administered both nasally and in emergencies also buccally.

In the following, the preferred embodiment of the inventive bi-dose nasal spray will be described. Using this bi-dose nasal spray, the active agent solution (preferably a midazolam solution but also fluid or powdery mixture) can be administered in a very short time in a safe, locally precise, fast acting way and independent of the position of the patient (e.g. upright, lying on the back or in lateral position), in a uniform fashion, independent of the spatial orientation of the nasal spray, without a prior preparatory action being necessary for activation at the spraying device (ready-to-use nasal spray device). This is most beneficial for healthcare professionals as well as for relatives and so far not available. This advantage of the orientation independent, position independent, safe and uniform application of medicines plays an important role both in the emergency treatment of patients with seizures and in the premedication of patients prior to diagnostic examinations such as MRI.

The locally precise, targeted administration of the active agent solution using the inventive nasal spray device is documented and verified by the following experimental tests and the data obtained therewith. This verification was done using a novel measurement procedure in connection with a high-resolution CT as imaging examination device, wherein other (tomographic) imaging procedures with appropriate spatial resolution or imaging quality, respectively, are possible. The novel examination procedure allows the characterization of nasal sprays in terms of their locally precise administration of the active agent (distribution of droplets) and, for the first time, allows the ad hoc evaluation of the efficacy of the application system, i.e. the analysis of the localization of the locally precise administration of a nasally administered active agent. As nasal sprays and nasal applicators, respectively, are used both locally and systemically, the distribution of the active agent, its surface distribution and its physical wetting of the mucosal surface has a significant influence on the efficacy of the system. As a gold standard, nuclear medicine methods (scintigraphy, SPECT, PET, possibly combined with MR or CT as fusion images)

are mostly used for the evaluation of the nasal deposition of nasally administered drugs with various applicators. However, these radiographic methods have important disadvantages in terms of their practical usability:

The spatial resolution (e.g. 3 to 5 mm, 5 to 10 mm, or 6 to 12 mm) is often limited.

From a temporal perspective, measurements must often be taken over a period of about 20 to 30 minutes which therefore cannot display short timeframes. The images thus show a superimposition of a longer time-frame with a confluence of the markers on the mucosal surface for about 30 minutes (gravitational force). Thus, the evaluation of the nasal deposition will be flawed. Due to the long measurement times no dynamic images are possible. The time course of the nasal distribution, and especially the initial distribution, thus cannot be displayed.

The image analysis is associated with a relatively high radiation exposure.

Nowadays, the preparation of detailed patient-specific nasal replicas based on radiological tomography examinations such as CT is possible [Warnken Z. N. et al.; "Personalized Medicine in Nasal Delivery: The Use of Patient-Specific Administration Parameters To Improve Nasal Drug Targeting Using 3D-Printed Nasal Replica Casts"; Mol. Pharmaceutics, 15, 1392-1402 (2018)]. In particular, the high-resolution patient-specific detection remains unclear in the nasal application whether an active agent reaches the desired places in the nasal cavities. The present invention now provides a method that allows the patient-specific detection of the locally precise deposition of an active agent in nasal application. In particular, the herein disclosed method, for any nasal sinuses and main cavities, allows the assessment whether and in which amount an active agent reaches them with the nasal application.

Computer tomography, abbreviated CT, is an imaging procedure in radiology that has a high spatial and temporal resolution in stratified imaging (3D acquisition). Based on the X-ray absorption profile of the object, the anatomic structure across individual layers can be displayed by CT images. From the absorption values of x-ray signals passing through the body computed slice images are generated. By technical improvements in the spatial resolution the image quality could be increased and thereby anatomic structures could be displayed in greater detail. Meanwhile, by means of novel techniques, low radiation examinations have been deployed in everyday clinical use. To better characterize and localize the nasal deposition on the nasal mucosa as well as across the various nasal cavities, a contrast agent (e.g. a iodine containing solution, a gadolinium containing contrast agent or other positively or negatively acting contrast agents) are filled into the nasal application system. Following the application into the nose (patient, test person, replica) by means of the nasal applicator, CT images are acquired. By means of the absorption profile across the whole nasal cavity, high contrast droplets can be depicted on the surface of the nasal mucosa and delineated from the surrounding tissue. The droplets appear with a significant contrast against the background that absorbs X-rays to a lower degree. The moisturizing of the surface but also the distribution of the high contrast fluid can thus be clearly depicted. In this way, the sprayed-in fluids can be localized and quantified relatively quickly after the application (X-ray absorption). The time course (dynamics) can be displayed. The iodinated contrast agents used are approved iodine containing solutions, suspensions or powders that vary with regard to their concentration, viscosity or osmolality. The person skilled in the art can select a contrast agent suitable for the application in an appropriate concentration and to possibly add this to midazolam or other active agents in case visualization is desired. In the present case, diluted solutions of iodinated contrast agents (e.g. Iopamiro®) with an iodine concentration of 92 mg/ml were used. In principle, all possible high contrast substances (fluid, solid, gaseous) can be used in varying concentration or dosage. In order to be able to characterize the basic properties of the nasal spraying device in a suitable way, one advantageously uses mixtures of substances that are similar to the pharmaceutically active agent solution to be used. Using solutions of iodinated contrast agents, aqueous solutions and their distribution are visualized in an optimal way. Powdery mixtures may be used as well for displaying and characterizing the nasal deposition of a nasal spray. As already mentioned, the inventive nasal spraying device allows a locally precise and volumetrically precise administration in any orientation (spatial orientation) of the nasal spray device. This was verified by the experiments described in the following and images were recorded (CT imaging procedure).

The characterization of nasal spraying devices is done by means of a computer tomographic nasal deposition technique. For this, the nasal spraying devices filled with solutions of aqueous iodine or other contrast agents must be used from various directions on a nose model (hereinafter also called nose replica).

The nose replica can be prepared in various ways. The nose model used in the experiments described below was designed based on human CT images and manufactured either by casting techniques or by 3D printing methods (even from various patients thus modeling the variable shapes of the nasal cavity). The nose model preferably consists of synthetic resins or of plastics selected in such a way that they do not produce any artifacts in CT imaging and allow an appropriate contrast between the applied iodine solution, fluid or powder and the anatomic structure of the model (different X-ray density between the surfaces of the replica and the contrast agent). Of advantage for displaying the surface deposition is the use of a replica that consists of a finely structured surface texture without surrounding tissue, possibly a model with a hydrophilic coating or a model bathed by air absorption.

For characterization of nasal spraying devices, the nose replica is brought into the desired position (tilted) and then stabilized. Due to the constant application angle, the spatial position of the nasal spraying device during administration is defined. Subsequently, the administration of the solution, fluid or powder of the active agent with the contrast agent ensures by means of the nasal spraying device to be examined. Immediately after the administration, the locally precise administration is localized by computer tomography or another imaging technique and is thereby characterized and verified. Due to the added contrast agent, the distribution of the droplets of the solution or fluid or the powdery particles, respectively of the active agent on the inner surface in the nasal cavity of the nose replica is clearly visible on the CT images or similar devices. In the present case it could be shown, based on the CT images in high resolution that the contrast agent spreads in the anterior and middle upper nasal cavity. Such measurements can also be done in an individual patient with ambiguous ENT conditions or for increasing the safety of the application.

The following preconditions are important in order to display and localize the orientation independent uniform timely (ready-to-use nasal applicator) nasal deposition with the inventive nasal sprays: use of a contrast agent containing substance (solution, mixture, powder, gas, emulsion etc., often with iodine containing contrast agents, gadolinium containing contrast agents or other high contrast substances) which can be filled into the nasal applicators or nasal sprays.

The application of the contrast agents with or without active agent shall ideally simulate or detect the nasal distribution, i.e. should have similar properties (flow, nebulization or surface charge) when being applied as possibly to be used pharmaceutical solutions, fluids or powdery mixtures of the active agent.

In addition, the nose replica should be suitable for CT measurements or similar examination procedures. In particular, the replicas must also allow quantification on the pixel level, i.e. with regard to the grid point (voxel level). For this the use of CT scanners or similar methods with the possibility to scan or display high resolution images must be ensured.

The nose model used in the present experiment consists of synthetic resins and/or plastics selected in such a way that they do not produce artifacts in CT imaging or possible alternative methods.

The nasal spray is filled with the iodine contrast agent containing solution, fluid or powder mixture, and the sprays are sprayed into the nostrils of the nose model in defined application angles (reference: nose bridge). The angle between the nasal sprays and the nose model should be kept constant (preferably physiological angles of introduction) so that the individual measuring points can be repeatedly measured and verified. The application is standardized by using a fixed holder for the nasal spray so that the measurements can be done in a reproducible way. Immediately after application of the solution, the fluid or the powdery mixtures by means of a spray, the image capture is started. The image capture is completed within a few seconds before a confluence of the deposited droplets, suspensions or powders (caused by the gravitational force) ensues. Thanks to the high temporal resolution of the CT device used, the position independence of the nasal application could be demonstrated (compare the images shown in FIG. 3). The CT scanner used in these experiments preferably has a high resolution (e.g. from 0.04 mm to 1 mm). At this resolution the anatomic structure of the nose as well as the droplets deposited onto the inner plastic surface of the nose model can be displayed in good quality.

The measured CT recordings must be processed using post processing methods (post processing techniques) for a better display of the contrast agent on the nasal mucosae having a low X-ray density. Various 3D techniques with a display of complete volumes as well as subtraction techniques are possible. In particular, one can subtract native images from the contrast images so that only the applied contrast agents can be displayed without background and anatomy. This allows displaying the anatomic structures separated from or superimposed by the contrast agent images. In the images shown in FIG. 3 CT recordings are shown in the various application positions (body standing, lying and so on) with the corresponding application angles. At first, a native image of the nose replica or model was taken before the application of a contrast agent (top left). The nose model shows no CT artifacts and the anatomic fine structure is well visible. The five other images each show a CT image capture after the application of the nasal sprays from the various angles. The depositions of the iodine containing droplets in the nasal cavity are shown as bright spots and are thus localized. From a qualitative perspective, all application directions lead to a similar distribution of the solutions, fluids or powders, respectively that were administered using the nasal spray.

The pixel (voxel) independent quantification of the deposited contrast agent (here an iodine containing contrast agent solution) is done by various methods known to the one skilled in the art (e.g. region growing method, Houndsfield unit threshold, iodine mapping, see e.g. Binh D B, Nakajima T, Otake H et al. Iodine concentration calculated by dual-energy computed tomography (DECT) as a functional parameter to evaluate thyroid metabolism in patients with hyperthyroidism in *BMC Medical Imaging* 2017; 17: 43).

The present invention therefore also relates to a method for qualitative and/or quantitative detection (localization) of the locally precise, preferably uniform administration of an active agent in a nasal application which is characterized in that the active agent is sprayed into a nose model or in vivo in a patient and the locally precise deposition of the fluid or the powder of the active agent is measured, localized and visualized using imaging methods, e.g. by the addition of contrast agents, fluorescent markers, dyes or other visualizable substances. Preferably the imaging method is a high resolution (<4 mm), low radiation, fast imaging method.

In one embodiment the qualitative and/or quantitative detection method is characterized in that the time course (dynamics) of the nasal distribution and the removal of the active, radiation absorbing agent is shown and quantified in real time.

In one embodiment the qualitative and/or quantitative detection method is characterized in that it can reconstruct volumetrically ("Volume Rendering") and show in high resolution in 2D/3D the surface structure of the nasal mucosa and nasal cavities.

In one embodiment the qualitative and/or quantitative detection method is characterized in that with the method, the patient-individual nasal deposition of an active agent can be localized and characterized qualitatively and quantitatively in a locally precise manner.

In one embodiment the nasal spray in accordance with the present invention is therefore characterized in that it has been shown by the qualitative and/or quantitative detection method mentioned above, that a targeted locally precise administration of the liquid of the active agent to the nasal mucosa of a patient is achieved irrespective of the position of the patient (standing upright, sitting, lying or in any intermediate position).

Using this detection method, it can be verified if a nasal spray meets or does not meet the requirement of a locally precise administration of a fluid or powder of the active agent onto the nasal mucosa of a patient. Preferably, the nasal spray complies with the locally precise, targeted and uniform administration irrespective of the orientation of the nasal spray during the spraying procedure (e.g. straight up, horizontally or straight down and in any intermediate position).

The detection method allows the qualitative and/or quantitative display of the nasal deposition of the solution, fluid or powder of the active agent after the spraying procedure in a reproducible way.

The dynamic recording in the replica can be done over several minutes or any period of time so that the secondary distribution, the possible removal via the ciliae as well as osmotic or other factors influencing the dynamics can be monitored, too.

Although the above-mentioned detection method is described using an artificial nose model, the detection method can also be carried out directly in vivo in a patient.

The detection method in humans (in vivo, patient or test person), insofar it is a CT method, preferably uses low radiation doses.

Preferably, the dynamic recording in humans (in vivo, patient or test person) is over a short period of time, e.g. over a time span of a few minutes.

The above-mentioned detection method can also be used to reconstruct and display in a better way the surface structure of the interfaces by means of special reconstruction techniques (3D). By the wafer-thin coating of the interfaces with iodine or other contrast substances via the nasal spray, preferably as bi-dose nasal spray device, the interfaces can be displayed in high resolution in a 3D or projection method. This allows a specific display of the mucosa and contour mapping.

The above-mentioned detection method can also be used for the personalized high-resolution detection with the aim to prove that an active agent reaches desired places in the nasal cavities after nasal application. Depending on the diverse patient-specific anatomic structure of the nose and the nasal cavities, it is suitable to qualitatively and quantitatively localize and determine in a locally precise fashion the nasal deposition of an active agent alone or in a powdery mixture, solution or fluid in a nasal application. In this case a detailed nose replica with the herein disclosed features is prepared from patient-specific radiological tomographic examinations (MRI/CT, SPECT or PET) of the nasal cavity. In an exemplary embodiment a nose replica can thus be designed based on CT recordings of humans and be produced either by casting techniques or 3D printing methods. The nose model preferably consists of synthetic resins or plastics that are selected in such a way that they do not produce artifacts in CT imaging and allow an appropriate contrast between the applied iodine solution, fluid or powder and the anatomic structure of the model (different X-ray densities between replica and contrast agent). Of advantage for the display of the surface deposition is the use of a replica consisting of a finely structure surface texture without surrounding tissue. Subsequently, the nasal deposition of the active agent is analysed and characterized with the method. In addition, the dynamic distribution of the active agent within a desired period of time may be characterized. This method allows the patient-specific verification of the suitability of a drug, a treatment or a nasal spraying device based on the high resolution and locally precise localization and characterization of the nasal deposition of an active agent in a patient-specific nose replica.

The present invention also relates to a nasal spray, preferably a bi-dose nasal spray with the features as mentioned above and characterized in that it is demonstrated with the above-mentioned method that a locally precise uniform possibly targeted administration of the active agent fluid or of an active agent powder on the nasal mucosa of a patient can be achieved with the nasal spray.

A nasal spray tested in this way allows the orientation independent nasal administration of a solution, fluid or powder of the active agent to a patient, preferably in medical emergencies and in cases where the administration is limited by spatial constrictions.

The above-mentioned method for airless filling and air-tight sealing of an active agent container for use in an inventive nasal spray can also be applied to other forms of active agent containers. Thus, the present invention also relates to a method for airless and airtight sealing of a container. The method is characterized in that the sealing of the container by inserting a plug into the container takes place in a closed system. Preferred containers are glass or plastic ampoules with a filling volume of up to 2 ml.

Preferably the sealing of the container is done in such a way that no or as little as possible air is left between the solution in the container and the plug.

Thus, the invention also relates to a method for airless and air-tight sealing of an active agent container for use in a nasal spray characterized in that inserting the plug into the active agent container is carried out in a closed system into which the active agent container with the solution of the active agent is inserted, wherein no air or as little air as possible remains between the solution of the active agent and the plug.

Preferably the method is carried out in a closed system consisting of a sealing chamber, a movable plunger and an outlet for aspirating the air in the closed system. A corresponding system and the corresponding procedure are schematically shown in FIG. 4a.

The invention claimed is:

1. A ready-to-use bi-dose nasal spray device for sedation, premedication, or treatment of patients with claustrophobia, anxiety disorders, panic attacks; or for the treatment of convulsions in CNS diseases consisting of four components:
   a) a drive element (A) including an actuator, including a spring and a hollow needle;
   b) a vial holder (B);
   c) an active agent container (C); and
   d) an air-tight sealing plug (D),
   whereby triggering of the nasal spray device is independent from air pressure by direct shift of the active agent container (C) against the air-tight sealing plug (D) by pressure to the drive element (A) whereby the hollow needle perforates the air-tight sealing plug (D);
   characterized in that
   i) the nasal spray device has a blocking system consisting of two blocking points (BP) in the vial holder (B) whereby a spraying mechanism is blocked at a first spray blocking point (BP1) and then again blocked at a second spray blocking point (BP2);
   ii) the active agent container (C) contains an aqueous solution or a liquid of midazolam or a salt thereof;
   iii) the active agent container (C) containing the aqueous solution or the liquid of the midazolam or the salt thereof is hermetically sealed with the air-tight sealing plug (D) so that as little as possible or no residual air is left in the active agent container (C);
   iv) the nasal spray device is configured to allow the administration of two doses consisting of a first spray-dose and a second spray-dose with each an equivalent, defined volume of the aqueous solution or the liquid of the midazolam or the salt thereof, and the aqueous solution or the liquid of the midazolam or the salt thereof is depleted after delivery of the second spray-dose so that no further spray of the ready-to-use bi-dose nasal spray device is possible; and
   (v) wherein the nasal spray device is configured to allow for an equal administration of the two doses, independent of a spatial orientation of the nasal spray device.

2. The ready-to-use bi-dose nasal spray device of claim 1, characterized in that the two doses can be administered with the nasal spray device without the nasal spray device having to be activated in advance.

3. The ready-to-use bi-dose nasal spray device of claim 1, characterized in that the nasal spray device indicates whether the first spray-dose has already been made with the nasal spray device.

4. The ready-to-use bi-dose nasal spray device of claim 1, characterized in that the nasal spray device indicates whether the second spray-dose has already been made with the nasal spray device.

5. The ready-to-use bi-dose nasal spray device of claim 1, characterized in that the active agent container (C) in the nasal spray device contains 215±15 µl, 230±10 µl, 225 ±10 µl, 225±5 µl, or 230 µl of the aqueous solution or liquid of the midazolam or the salt thereof.

6. The ready-to-use bi-dose nasal spray device of claim 1, characterized in that with each dose of the nasal spray device, a volume of 75, 80, 90, 100, 110, 120, 125, 130, 140, or 150 µl with a range of the volume of ±25% each of the aqueous solution or liquid of the midazolam or the salt thereof can be administered.

7. The ready-to-use bi-dose nasal spray device of claim 1, characterized in that with each dose of the nasal spray device, a volume of 100±15 µl, 100±10 µl, or 100±5 µl, or 100 µl of the aqueous solution or liquid of the midazolam or the salt thereof can be administered.

8. The ready-to-use bi-dose nasal spray device of claim 1, characterized in that with each dose of the nasal spray device, either
 a) 0.25 to 5 mg of the midazolam or the salt thereof can be administered; or
 b) 1.0 to 10 mg of the midazolam or the salt thereof can be administered.

9. The ready-to-use bi-dose nasal spray device of claim 1, characterized in that with each dose of the nasal spray device, either
 a) 0.278 mg to 5.56 mg midazolam HCl corresponding to 0.25 mg to 5 mg midazolam base can be administered; or
 b) 1.11 mg to 11.12 mg midazolam HCl corresponding to 1 mg to 10 mg midazolam base can be administered; or
 c) 0.02 mg to 0.5 mg midazolam per kg body weight of a patient can be administered.

* * * * *